(12) United States Patent
Dal Sasso et al.

(10) Patent No.: US 7,671,988 B2
(45) Date of Patent: Mar. 2, 2010

(54) DETECTION OF PARTICLES

(75) Inventors: Robert Dal Sasso, South Yarro (AU); David Logan, Box Hill (AU); William Phelan, Box Hill North (AU)

(73) Assignee: American Ecotech LLC, Warren, RI (US)

( * ) Notice: Subject to any disclaimer, the term of this patent is extended or adjusted under 35 U.S.C. 154(b) by 336 days.

(21) Appl. No.: 11/539,878

(22) Filed: Oct. 10, 2006

(65) Prior Publication Data

US 2007/0127021 A1   Jun. 7, 2007

Related U.S. Application Data

(63) Continuation-in-part of application No. 10/906,160, filed on Feb. 4, 2005, now abandoned.

(60) Provisional application No. 60/521,079, filed on Feb. 18, 2004.

(51) Int. Cl.
    *G01N 21/00* (2006.01)
(52) U.S. Cl. ............ 356/338; 250/559.44; 250/559.49; 356/337; 356/446
(58) Field of Classification Search ......... 356/337–343, 356/417, 369, 446; 250/559.44, 559.49
    See application file for complete search history.

(56) References Cited

U.S. PATENT DOCUMENTS

| | | | |
|---|---|---|---|
| 4,541,719 A * | 9/1985 | Wyatt ..................... 356/343 |
| 5,461,476 A | 10/1995 | Fournier ..................... 356/346 |
| 5,751,423 A | 5/1998 | Traina et al. ................ 356/338 |
| 6,020,961 A | 2/2000 | Moore ........................ 356/338 |
| 6,055,052 A | 4/2000 | Lilienfeld .................... 356/338 |
| 6,084,680 A | 7/2000 | Tuunanen et al. ........... 356/417 |
| 6,154,277 A * | 11/2000 | Snelling et al. ............. 356/338 |
| 6,330,519 B1 | 12/2001 | Sawatari ..................... 702/127 |
| 6,836,332 B2 * | 12/2004 | Mosley et al. ................. 356/73 |
| 6,975,404 B2 * | 12/2005 | Schwarz ..................... 356/446 |
| 7,016,053 B2 | 3/2006 | Moriuchi et al. |
| 7,157,694 B2 * | 1/2007 | May et al. ................... 250/228 |
| 7,177,033 B2 | 2/2007 | Yoshida |
| 7,290,893 B2 | 11/2007 | Amphlett |
| 7,303,308 B2 | 12/2007 | Amphlett |
| 7,488,965 B2 * | 2/2009 | Cochran et al. .......... 356/240.1 |
| 2005/0156103 A1 | 7/2005 | May et al. ................... 250/228 |
| 2005/0162737 A1 | 7/2005 | Whitehead et al. .......... 359/454 |

* cited by examiner

*Primary Examiner*—Gregory J Toatley, Jr.
*Assistant Examiner*—Iyabo S Alli
(74) *Attorney, Agent, or Firm*—Salter & Michaelson (57) ABSTRACT

A device (10) is provided for measuring at least one characteristic (12) related to presence of particles. The device (10) includes a light source unit (16) for emitting light into a region (18) containing particles (20), with the light source being configured to emit light from a plurality of locations in a manner so that the emitted light follows a desired intensity distribution (22), the desired intensity distribution (22) being desired for the measurement of the at least one characteristic (12). In preferred embodiments the intensity distribution is Lambertian.

23 Claims, 10 Drawing Sheets

Angular Response.

Angular Response Data.

| IDEAL INTENSITY | | | | | | | | MEASURED INTENSITY | | | | | | | |
|---|---|---|---|---|---|---|---|---|---|---|---|---|---|---|---|
| ANGLE | | | | | | | | ANGLE | | | | | | | |
| 0 | 0.001 | 50 | 0.306 | 95 | 0.398 | 14 | 0.257 | 0 | 0.001 | 50 | 0.308 | 95 | 0.4 | 140 | 0.253 |
| 5 | 0.035 | 55 | .0328 | 100 | 0.394 | 14 | 0.23 | 5 | 0.024 | 55 | 0.332 | 100 | 0.394 | 145 | 0.225 |
| 10 | 0.07 | 60 | 0.346 | 105 | 0.386 | 15 | 0.2 | 10 | 0.062 | 60 | 0.351 | 105 | 0.387 | 150 | 0.199 |
| 15 | 0.104 | 65 | 0.362 | 110 | 0.376 | 15 | 0.169 | 15 | 0.104 | 65 | 0.365 | 110 | 0.376 | 155 | 0.166 |
| 20 | 0.137 | 70 | 0.376 | 115 | 0.362 | 16 | 0.137 | 20 | 0.142 | 70 | 0.377 | 115 | 0.361 | 160 | 0.132 |
| 25 | 0.169 | 75 | 0.386 | 120 | 0.346 | 16 | 0.104 | 25 | 0.173 | 75 | 0.386 | 120 | 0.346 | 165 | 0.095 |
| 30 | 0.2 | 80 | 0.394 | 125 | 0.328 | 170 | 0.07 | 30 | 0.203 | 80 | 0.393 | 125 | 0.324 | 170 | 0.054 |
| 35 | 0.23 | 85 | 0.398 | 130 | 0.306 | 175 | 0.035 | 35 | 0.233 | 85 | 0.398 | 130 | 0.303 | 175 | 0.02 |
| 40 | 0.257 | 90 | 0.4 | 135 | 0.283 | 180 | 0.001 | 40 | 0.258 | 90 | 0.4 | 135 | 0.28 | 180 | 0.002 |
| 45 | 0.283 | | | | | | | 45 | 0.281 | | | | | | |

LIGHT DISTRIBUTION OF LIGHT SOURCE WITH AND WITHOUT GLASS DIFFUSER

DETECTION OF PARTICLES

RELATED APPLICATIONS

This is continuation-in-part of U.S. application Ser. No. 10/906,160 filed Feb. 4, 2005, now abandoned which claims the benefit of U.S. Provisional Application No. 60/521,079 filed Feb. 18, 2004.

FIELD OF INVENTION

The present invention relates to the detection of particles. In preferred arrangements the present invention provides nephelometers for measuring visibility.

The disclosure of PPA Application No. 60/521,079 filed on Feb. 18, 2004 and U.S. application Ser. No. 10/906,160, filed Feb. 4, 2005 are hereby fully incorporated by reference.

BACKGROUND ART

The discussion throughout this specification comes about due to a realisation of the inventors and/or the identification of certain prior art problems by the inventors.

A nephelometer is an instrument sometimes used for measuring characteristics of particles suspended in a fluid. In operation a nephelometer uses a light source to emit light into a region occupied by a fluid. Following this, light scatters off particles suspended in the fluid and is subsequently received by a detector. The detector converts the received light into one or more electrical signals allowing for characteristics such as the density of the particles suspended in the fluid to be determined. This is preferred using a predetermined algorithm.

In situations involving atmospheric air quality, nephelometers are sometimes used to provide measures relating to visibility. With water quality testing, nephelometers are sometimes can be to measure characteristics such as turbidity. Other types of nephelometers are used in the detection of particles produced by combustion. The present invention is not to be taken as being limited to nephelometers.

The inventors have realised that nephelometers suffer from several problems, and have sought to provide an improvement, or at least to provide the public with a useful choice.

Any discussion of documents, devices, acts or knowledge in this specification is included to explain the context of the invention. It should not be taken as an admission that any of the material formed a part of the prior art base or the common general knowledge in the relevant art in the relevant jurisdiction on or before the priority date of the disclosure and claims herein.

SUMMARY OF INVENTION

According to a first aspect of the present invention there is provided a device for measuring at least one characteristic related to presence of particles, the device comprising: a light source unit for emitting light into a region containing particles, wherein the light source is configured to emit light from a plurality of locations in a manner so that the emitted light follows a desired intensity distribution, the desired intensity distribution being desired for the measurement of the at least one characteristic.

Preferably each of the plurality of locations is spaced apart along an arc. The arc may be semicircular and the light that is emitted from the plurality of locations may be directed from the plurality of location towards a focal region defined by the arc.

Advantageously a diffuser is located at the focal region for smoothing the emitted light so that the emitted light follows the desired intensity distribution.

The light source unit may comprise an array of spaced apart light emitting diodes and the light emitted from the plurality of locations may follow a Lambertian distribution desired for the measurement of the at least one characteristic. Such a preferred arrangement is particularly advantageous for use in nephelometer visibility measurements.

The device may include a temperature compensation unit for controlling the intensity of light in response to variations in temperature and a light compensation unit for varying the intensity of light provided from each of the light emitting diodes in response to one of the diodes failing.

The light source unit may comprise at least one array of spaced apart light emitting diodes, the diodes being adapted to provide a desired intensity distribution using a selected one of plurality of light emitting diode wavelength ranges. The plurality of light emitting diode wavelength ranges may comprise a red light emitting diode wavelength range, a blue light emitting diode wavelength range and a green light emitting diode wavelength range. Arrangements of the present invention may provide one, two or three separate arrays of light emitting diodes of different wavelengths without having to remove the light source. The light emitting diodes may be mounted on the same circuit board in a sequential alternating manner in the same plane. Alternatively the light emitting diodes may be mounted on the same circuit board in separate planes. In some arrangements three arrays of light emitting diodes of the same wavelength are provided in three corresponding spaced apart planes. In one operating mode the arrays may be operated simultaneously should the need for additional light intensity be required.

Characteristics that are able to be measured by the present invention include visibility, as well as other characteristics related to the presence of particles. These could include particulate scattering coefficients at one, two or three wavelengths, particulate backscattering coefficients at one, two or three wavelengths, characteristics of aerosol particle size distribution, particulate mass concentration and so forth. Temperature, humidity and barometric pressure are further examples that may be measured in say an arrangement of the invention providing a nephelometer device. The present invention is not to be taken as being limited to the above examples.

Nephelometers have previously employed single light sources when measuring visibility characteristics. Whilst these sources do follow a Lambertian distribution, to some relatively small degree, they are not able to provide the same sensitivity as preferred arrangements of the present invention. Preferred nephelometer arrangements according to the present invention are accordingly considered advantageous.

According to a second aspect of the invention there is provided a device for measuring at least one characteristic related to the presence of particles, the device comprising: a light source unit for emitting light into a region containing particles, a detection unit for receiving light scattered by the particles, wherein the light source unit comprises a plurality of spaced apart light emitting diodes and a control unit, the control unit for controlling the intensity the light emitted by each of the spaced apart light emitting diodes, according to the disposition of each light emitting diode, such that the emitted light follows a desired Lambertian intensity distribution, the desired Lambertian intensity distribution being desired for the measurement of the at least one characteristic.

According to a third aspect of the invention there is provided a method of measuring at least one characteristic related to the presence of particles, the method comprising: emitting light into a region containing particles, wherein the light is emitted into the region from a plurality of locations such that the emitted light follows a desired intensity distribution, the desired intensity distribution being desired for the measurement of the at least one characteristic.

Preferably the method includes controlling the intensity of the individual light emitting diodes to vary overall light intensity. Controlling the intensity of the individual light emitting diodes may include tuning the diodes on and off.

Preferably the light is emitted from each of the plurality of locations in pulsed manner so that a relatively greater intensity output can be achieved without damaging the light source unit.

According to a fourth aspect of the present invention there is provided a method for measuring at least one characteristic related to the presence of particles, the device comprising: emitting light from a plurality of spaced apart light emitting diodes into a region containing particles, detecting light scatted by the particles, and controlling the intensity the light emitted by each of the spaced apart light emitting diodes, said control being according to the disposition of each light emitting diode, such that the emitted light follows a desired Lambertian intensity distribution, the desired intensity distribution being desired for the measurement of the at least one characteristic.

According to another aspect of the invention there is provided a method of providing an illumination within a predetermined area, the method comprising: providing a plurality of sources of illumination; and controlling the intensity of at least one of the illumination sources such that the intensity of the illumination provided by the sources is substantially Lambertian.

According to another aspect of the invention there is provided a method of calibrating a nephelometer having a light source unit, the method including calibrating the light source by driving light source elements of the light source at a portion their maximum intensity, in order to calibrate the intensity output of the nephelometer without damaging the elements. Driving the light emitting diodes at a portion of their maximum intensity allows for advantageous calibration of the light source. As would be apparent the closer the Lambertian distribution is to an 'ideal' distribution the less error there will be in the results.

Other aspects and preferred aspects are disclosed in the specification and/or defined in the appended claims, forming a part of the description of the invention.

Particularly preferred arrangements of the present invention have been found to result in a number of advantages, such as: improved particle characteristic measurement sensitivity using a very stable light source which produces a fixed wavelength of light with a distribution that is substantially Lambertian; low maintenance since the light source is more easily cleaned than other alternative light sources; a light source having a very long life time in comparison to other light sources which require more regular cleaning and replacement; the ability to quickly change the light source light wavelength by switching in and out different self contained arrays of light emitting diode's, with the same microprocessor being able to be reused and adjust automatically for each different array; and an improved Lambertian light distribution than achieved by alternative light sources without the need for additional cooling or heat dissipation. Further advantages are detailed below.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, objects, advantages and aspects of the present application may be better understood by those skilled in the relevant art by reference to the following description of preferred embodiments taken in conjunction with the accompanying drawings, which are given by way of illustration only, and thus are not limitative of the present invention, in which.

DETAILED DESCRIPTION

Figure 1:
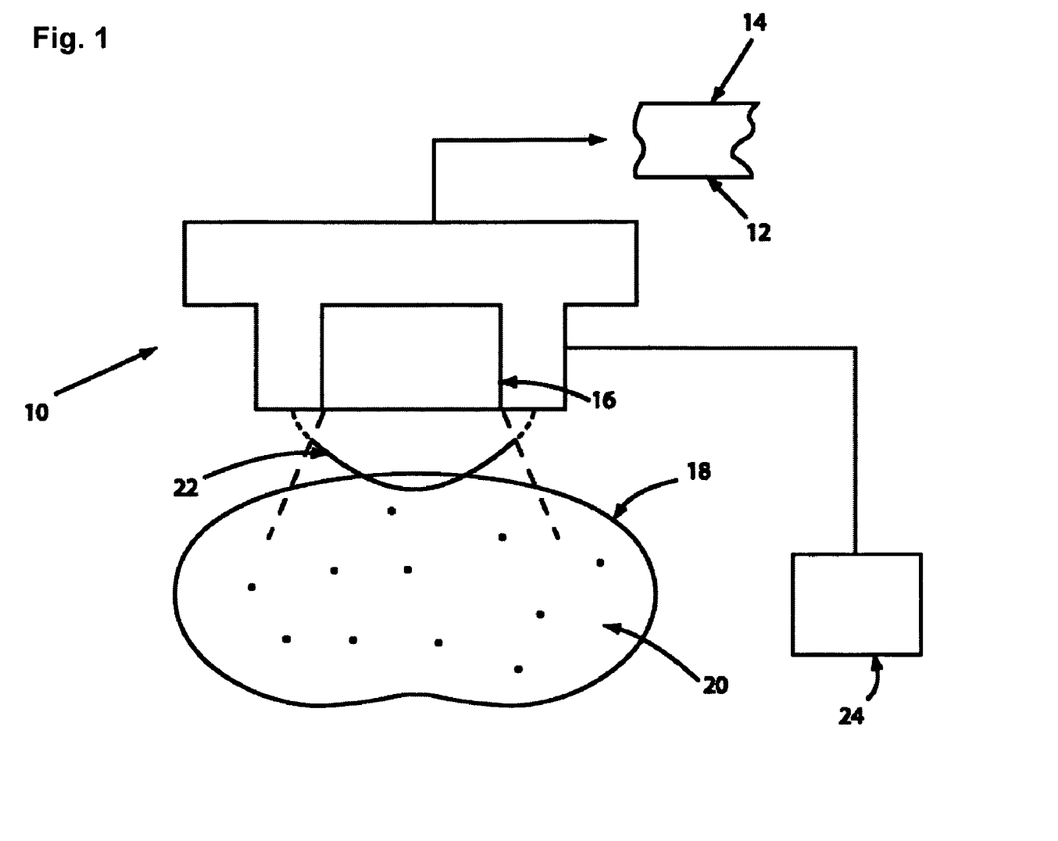
FIG. 1 is a schematic view of a device according to a first preferred embodiment of the present invention.

Referring to FIG. 1 there is shown a device 10 according to a first preferred embodiment of the invention.

The device 10 is able to provide a Lambertian concentrated light source in that the device 10 is configured to emit light following a cosine distribution output as a function of angle. In the arrangement the angle over which the cosine distribution is followed spans over 5 to 175 degrees. In this manner the device 10 provides light following a Lambertian distribution.

Advantageously the device 10 follows a Lambertian distribution with greater accuracy, in comparison to prior art devices. This provides for the ability to make measurements with increased accuracy.

In the embodiment, the device 10 is provided for measuring at least one characteristic 12 related to presence of particles. The at least one characteristic 12 comprises an atmospheric visibility measurement 14. The device 10 includes a light source unit 16 for emitting light into a region 18 containing particles 20, with the light source being configured to emit light from a plurality of locations in a manner so that the emitted light follows a desired intensity distribution 22, the desired intensity distribution 22 being desired for the measurement of the at least one characteristic 12.

A detection unit 24 is provided as part of the device 10. The detection unit 24 is positioned at an angle for receiving light scattered by the particles 20 for use in the measurement of the at least one characteristic 12.

Figure 6:
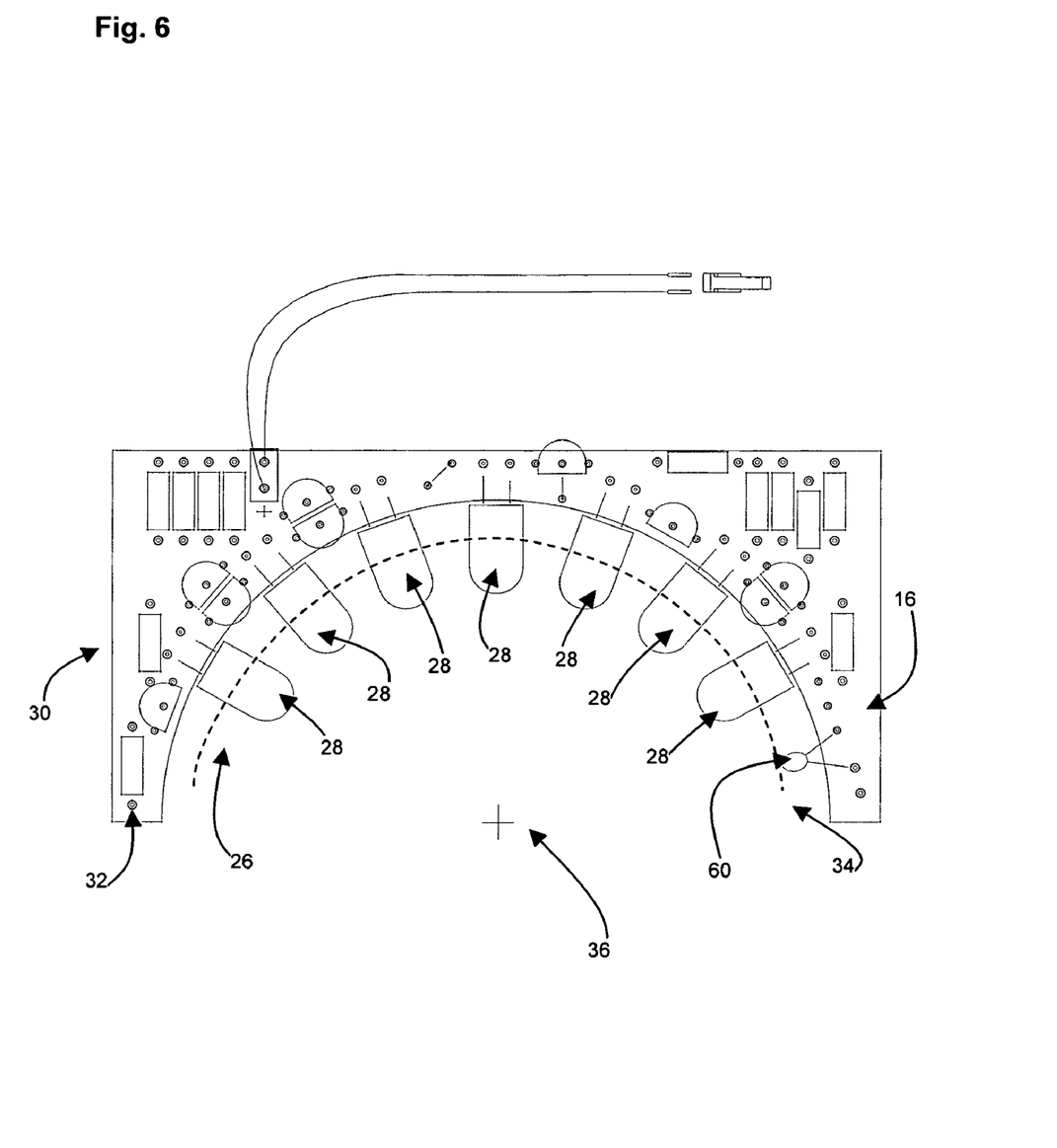
FIG. 6 is a perspective view of the light source unit shown in FIG. 2.

FIG. 6 provides a schematic side view of the light source unit 16. The light source 16 constitutes an embodiment of the present invention in its own right.

As is shown in FIG. 6, the light source unit 16 includes an array 26 of spaced apart light emitting diodes 28. As such the light source unit 16 is configured so that each of the light emitting diodes 28 provide an intensity of light in which the emitted light follows the desired intensity distribution 22.

A control unit 30 is provided as part of the light source unit 16 the control unit includes in the form of a circuit 32 which provides particular currents to each of the light emitting diodes 28.

In the embodiment the light emitting diodes 28 are high intensity light emitting diodes 28 arranged along an arc 34.

The arc 34 is semi-circular and the light emitting diodes 28 are each directed towards a focal region 36 about which the light emitting diodes 28 are arranged. In this particular embodiment the focal region 36 is the focal point of the arc 34. In other embodiments the focal region spans over an area.

The device 10 includes a diffuser 52 for diffusing light emitted by the diodes 28. The diffuser 52 is disposed in front of the diodes 28 so that the light emitted from the diodes 28 is smoothed to follow the Lambertian distribution.

Figure 11:
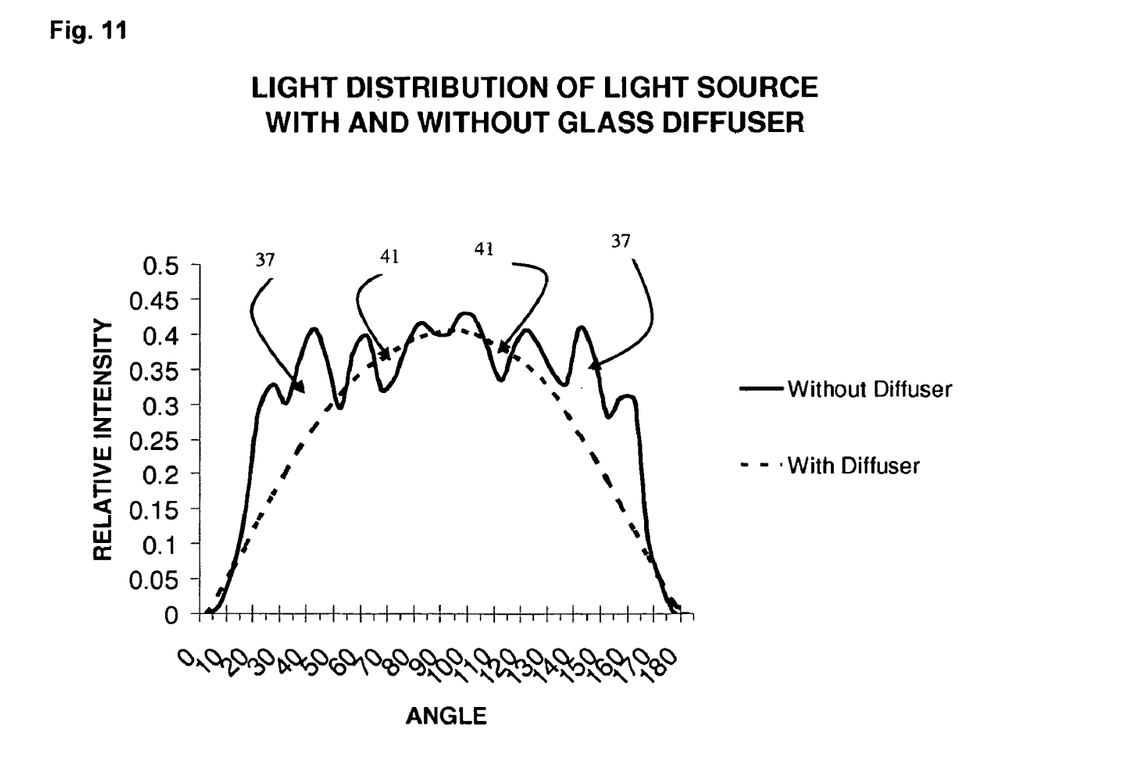
FIG. 11 is a graphical view representing how a device according to an embodiment of the invention follows an ideal Lambertian distribution.

As would be apparent to a person skilled in the art, light emitted directly from the light emitting diodes 28 in the arc 34 would have several regions of relatively pronounced intensity respectively corresponding to each of the light sources 28. This illustrated in FIG. 11 which shows a light distribution of a light source according to a similar embodiment, with and without a diffuser in front of light emitting diodes. As shown in the Figure the diffuser operates to smooth regions 37 of relatively pronounced intensity such that the intensity provided follows a Lambertian distribution. FIG. 11 also shows regions 41 of relatively low intensity, which are also smoothed. Thus, the diffuser 52 operates to smooth the emitted light from the diodes such that the desired Lambertian distribution, that is distribution 22, is provided.

By positioning the diffuser 52 at the focal point, where the light emitting diodes 28 are focused, the diffuser 52 is able to advantageously distribute the incident light over 170 degrees from the diffuser, in a relatively even fashion. This is particularly advantageous and assists in the provision of the intensity distribution 22. A very high concentration of light is provided at the focal point 36 by directing the light emitting diodes towards the focal point 36.

The diffuser is formed of glass and is masked around the focal point 36 so that the resulting area of the source is reduced. Whilst in the present embodiment the diffuser is fully exposed, in other embodiments the diffuser is masked around the focal point so as to leave a smaller rectangular aperture for the light to pass through. The advantage of these embodiments is so that the resulting source of light comes from a smaller area around the focal point. Other masking shapes are envisaged, however the rectangular shape is preferred to provide the Lambertian distribution in a plane along the plane of light emitting diodes.

Figure 2:
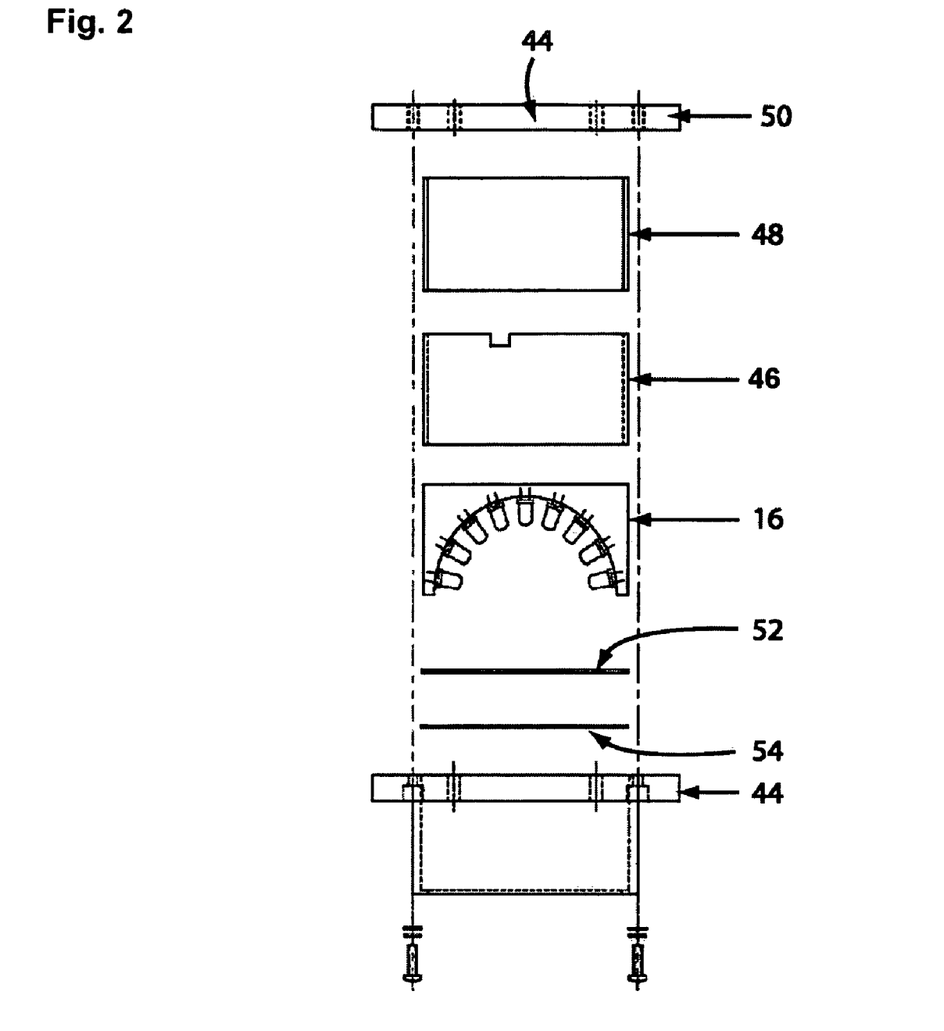
FIG. 2 is an exploded front view a light source unit used in the device illustrated in FIG. 1.
Figure 3:
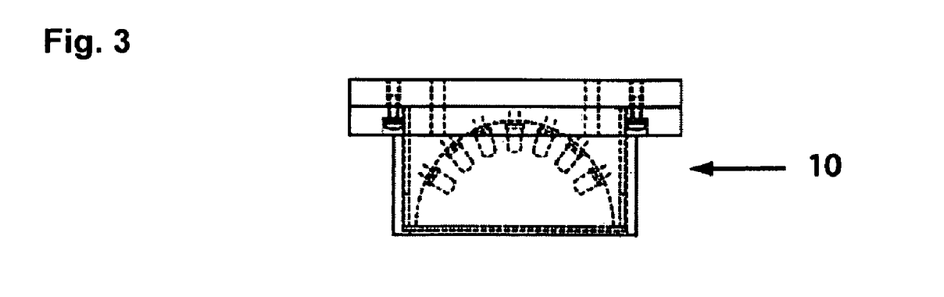
FIG. 3 is a side view of the light source unit shown in FIG. 2 with several internal elements of the unit being shown in phantom.
Figure 4:
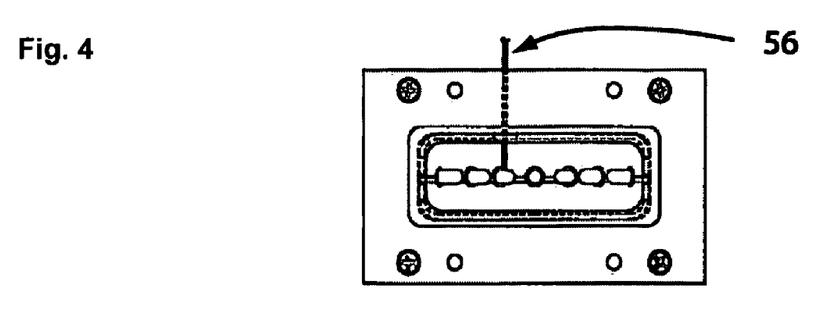
FIG. 4 is an underneath plan view of the light source unit shown in FIG. 2.
Figure 5:
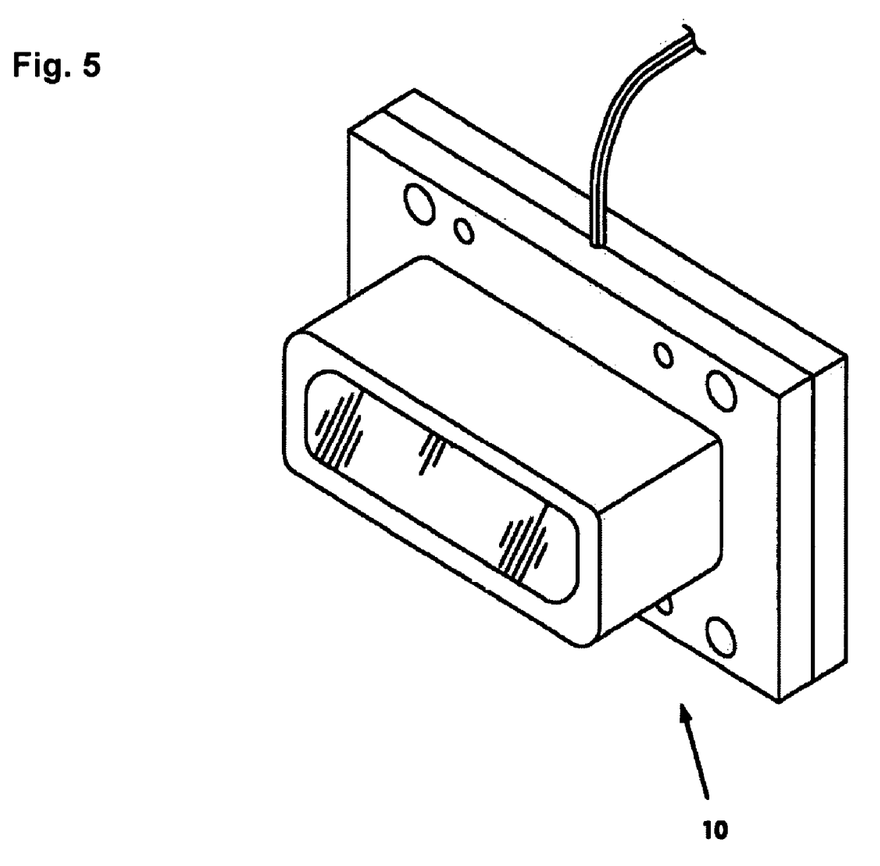
FIG. 5 is schematic side view of the light source unit shown in FIG. 2.

As described the light emitting diodes 28 are arranged in a semi-circular arrangement 34, falling substantially in a plane. The diodes 28 form part of a light emitting diode printed circuit assembly which provides, at least in part, control unit 30. The printed circuit board 32 includes transistors q1 to q10 and resistors r1 to r12. The light emitting diodes are designated LED2 to LED8. The cable 56 is connected directly to the printed circuit board 32.

The printed circuit assembly is mounted inside a light source housing 44 and includes of a printed circuit assembly mounting bracket top 46 and mounting bracket bottom 48. A housing top plate 50 is used to seal the light emitting diodes 28 between the top plate 46 and the light diffuser 52. In the device 10 the light diffuser 52 is sealed with sealant 54. The light source housing 44 provides a means by which the printed circuit assembly is mounted and sealed. The mounting brackets 46 and 48 keep the circuit board stable and serve to assist with limiting any heating effects on the ambient air.

The housing 44 is made of aluminium and is black anodised as well as having a coating of matte black paint in certain locations to reduce the effects light reflections. A cable 56 is provided for power purposes. The housing 44 and the sealant 54 serve to pneumatically seal the electronic components from the ambient air.

The array 26 comprises seven light emitting diodes 28 each of very high output intensity. These high output intensity diodes are super bright light emitting diodes.

The light emitting diodes 28 are chosen for not only their very bright output, but also their wavelength. It has been seen that with such light emitting diodes a wavelength output, typically at 520 nm, is very stable and should not vary by more than 30 nm. Other wavelengths can be achieved by using different wavelength light emitting diodes such as 700 nm for Red and 450 nm for Blue.

It is to be recognised that if the light output intensity of each light emitting diode was the same, then the combined output distribution of the light source would not be Lambertian. To provide a Lambertian distribution the control unit 30 individually sets the current through each of the light emitting diodes 28.

In this embodiment, the control unit 30 keeps the light intensity of each light emitting diode 28 very stable by proportionally controlling the amount of current flowing through the each light emitting diode. Whilst the light emitting diodes 28 have a narrow beam width angle of about 15 degrees circuitry provided by control unit 30 individually controls the current through each light emitting diode. Even though most of the light energy is focused in one spot, the combined output distribution of the light source is controlled such that after having passed thorough the diffuser 52 the intensity distribution is substantially Lambertian.

Put more simply each light emitting diode 28 is given a discrete driving current depending on the disposition of the light emitting diode so that the combined intensity effect of all the light emitting diodes 28 in combination is Lambertian.

In determining the current to supply to the light emitting diodes 28 the device 10 is run in a calibration mode where the light emitting diodes are driven continuously at about half their intensity setpoint (un pulsed) in order to calibrate the intensity output without damaging the light emitting diodes. In this manner the light source is calibrated by driving light source elements of the light source at a portion their maximum intensity in order to calibrate the intensity output without damaging the elements. It is to be appreciated that in some embodiments this is achieved using an external power source. In other embodiments the control circuit does this as part of a calibration process. Advantageously the calibration mode operates as a safety feature so as not to damage the light emitting diodes during calibration.

To vary the overall intensity of the light source unit 16 the drive voltage to light source unit 16 is increased and the subsequent current through each light emitting diode varies accordingly. The variation in the current supplied to each light emitting diode current is controlled so as to maintain a Lambertian light distribution.

In another embodiment have many more individual light emitting diodes varying the overall intensity of the light source is achieved by either varying the currents in each light emitting diode and by turning on and off individual light emitting diodes such that they are either contributing to the overall light intensity or not. This is a particularly notable feature of such embodiments.

Another feature, which is embodied by device 10, is that the overall output intensity of the light source unit 16 is calibrated to a standard pre-determined intensity so that the light source 16 can be replaced with a different similarly calibrated light source of the same standard predetermined intensity and which accordingly will exhibit similar characteristics.

This serves to assist in replacing a light source in a nephelometer or other instrument used for particulate monitoring. The common predetermined intensity is set within the device itself is preferably one of a group of standard predetermined intensities.

In the device 10 increases in temperature are controlled with a temperature compensation circuit provided in control unit 30 so that the output intensity of the light source is suitably compensated with changes in ambient temperature. The temperature compensation unit controls the intensity of light in response to variations in temperature.

Because light emitting diodes are very efficient, there is minimal heating of the light source from the light emitting diodes 28.

Figure 7:
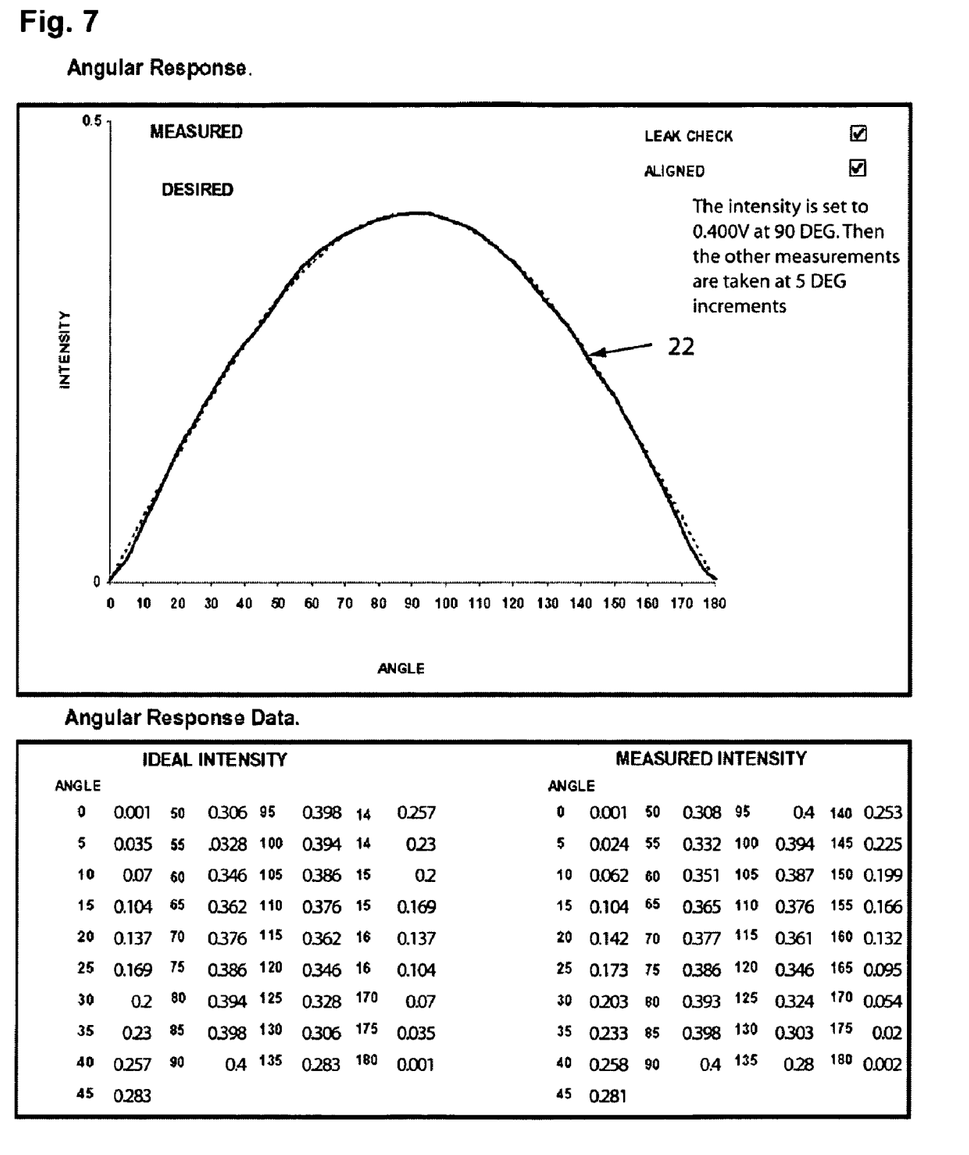
FIG. 7 is a graphical view representing how the device shown in FIG. 1 follows an ideal Lambertian distribution.

In experiments, the device 10 has been shown to provide a Lambertian concentrated light source of a high accuracy. This is shown in FIG. 7 where experimental data is provided. The data shows that the device 10 accurately approximates an ideal Lambertian light source by providing a cosine distribution output as a function of angle. On a careful examination of the data in the table provided in FIG. 7 it is apparent that the device 10 follows an ideal Lambertian light source distribution 22 in a highly accurate manner over a range of 5 to 175 degrees.

The device 10 is provided as an integrating nephelometer 10. This specific application is particularly advantageous as a highly accurate Lambertian distribution 22 is most desirable for measurement calculation purposes. Whilst this is a particularly advantageous application it is to be appreciated that arrangements of the light source unit 16 may be used for other applications, including future applications yet to be developed. In the arrangement described the detection unit 24 includes a photon multiplier tube which forms part of the nephelometer.

It is to be recognised that the Lambertian distribution does not have to extend over a particularly wide angle range but may, in embodiments be limited to a relatively narrow angle range in the order of even say 80 to 110 degrees.

It is to be appreciated the use of light emitting diodes is advantageous as the light output intensity of the light source unit 16 is very stable and does not vary appreciably with temperature changes. The use of light emitting diodes 28 also advantageously keeps radiated heat to a relatively minimal amount and means that the light source unit 16 has relatively small power consumption.

The detection unit 24 in the integrating nephelometer 10 includes a photomultiplier tube. The light source unit 16 advantageously provides a cosine distribution wavelength as a function of angle over an angle range of 5 to 175 degrees. In addition accuracy is improved by the production of relatively minimal radiant heat with relatively minimal power consumption.

Each of the diodes 28 emits light of wavelengths within a relatively narrow bandwidth, with a light output intensity that is very stable and does not significantly vary with temperature changes.

The nephelometer 10 provided as a result of each of these features is highly accurate, and in particular configurations is provided at relatively low cost and with relatively minimal maintenance requirements. Experimental arrangements have been used successfully as integrating nephelometers to enable a more highly accurate continuous measurement of the light scattering coefficient of fine particulates in an air sample, and thus providing an accurate and moreover, useful measure of ambient air quality.

In the past, some integrating nephelometers have utilized high intensity incandescent flash lamps in combination with various colour filters in order to create a specific wavelength light source. These types of nephelometers are prone to regular maintenance requirements, are expensive to replace, and are less accurate. Furthermore, and in contradistinction to the embodiment, the length of light source flash time is relatively small, which means that a reading of visibility must be taken quickly. The present embodiment is able to achieve several improvements by incorporating light emitting diodes into a nephelometer. Only relatively recently have light emitting diodes been manufactured that can emit a high enough intensity in order to operate effectively in a nephelometer of the present kind.

As could be apparent, it is possible to manually calibrate the currents which the circuit 32 provides to each of the light emitting diodes 28, by altering resistances within the circuit 32. The present embodiment additionally includes a micro control circuit as part of the control unit 30 for automatically varying the currents with user input. The micro control circuit is advantageously able to receive signals from a remote unit, such as the main microprocessor on the nephelometer, during the provision of a light such that light intensity distribution meets certain predetermined desirable criteria.

In the arrangement the micro control circuit is able to control the individual light emitting diode intensities by receiving remote instructions to vary electronic digital potentiometers. This improves the speed of calibration as the electronic circuit does not need to be manually modified in order to change the intensity of the light emitting diodes. In yet further embodiments control of the currents occurs automatically without remote interaction.

The light source unit 16 in the device 10 includes a temperature unit which provides a measure of temperature. The measure of the temperature is provided to the control unit 30 which controls the current supplied to each of the light emitting diodes 28 so that the output intensity of the light source unit 16 does not vary appreciably with variations in temperature. The temperature unit is able to compensate for both internal and external temperatures. In the device 10 a temperature element 60 is provided for the measurement of temperature. The element 60 comprises a thermistor.

The light source unit 16 further includes a light source compensation unit that is able to automatically compensate for any potential alteration in light intensity in the event of the characteristics changing of one or more individual light emitting diodes 28. This is achieved with the nephelometer microprocessor adjusting the drive voltage to the control unit 30 which in turn moderates the current provided to each remaining light emitting diode 28 in the array 26, ensuring that the total light intensity remains relatively constant. The light source compensation unit varies the intensity of light provided from each of the light emitting diodes in response to characteristics of one or more of the diodes varying.

The use of high efficiency light emitting diodes is of benefit in that there is relatively minimal heating of the light emitting diodes themselves. As a result additional cooling and heat dissipation units can, in some, embodiments, be avoided with the temperature compensation circuit ensuring that the output intensity provided does not vary appreciably with changes in ambient temperature. The use of LEDS has several concomitant advantages over halogen lamps and laser type sources.

Light emitting diodes are available in red, green, and blue, and have turn-on times well below one microsecond. Until recently, luminance and light output of light emitting diodes was not sufficient to obtain strong performances as an intense light source. Furthermore the use of light emitting diodes provides for the ability to measure continuously with much increased flash length capabilities. This is an appreciable advantage over prior art nephelometers.

It is to be appreciated that in the embodiment there is provided a device 10 for measuring at least one characteristic 12 related to the presence of particles 20. The device 10 comprises a light source unit 16 for emitting light into a region containing the particles 20. A detection unit 24 is provided for receiving light scattered by the particles 20 and the light source unit 16 comprises a plurality of spaced apart light emitting diodes 28 and a control unit 30. The control unit 30 is arranged for controlling the intensity the light emitted by each of the spaced apart light emitting diodes 28, according to the disposition of each light emitting diode 28, such that the emitted light follows a desired intensity distribution 22, the desired intensity distribution 22 being desired for the measurement of the at least one characteristic. The light emitting diodes 28 are disposed along a semi-circular arc 34 that is directed towards a focal point of the arc 34.

Thus, there is provided a light emitting diode source array comprising circuitry control of individual light emitting diode's to provide an accurate and continuous fixed wavelength frequency light source, that closely approximates a Lambertian distribution and which is suited for use in nephelometry, or other related applications.

In this particular application the device 10 allows for accurate measurement of the light scattering of particulate matter in order to provide a continuous measurement of air quality, and also provides for low maintenance, precision, and long life operation.

A further embodiment of the present invention involves the following operations. The embodiment comprises a method in which a first operation includes emitting light into the region 18 containing particles 20. After this the method comprises detecting light scattered by the particles 20. In the method the light is emitted into the region from a plurality of locations such that the emitted light follows a desired intensity distribution, the desired intensity distribution being desired for the measurement of the at least one characteristic. The locations from which the light is emitted are spaced apart along a semicircular arc.

Figure 10:
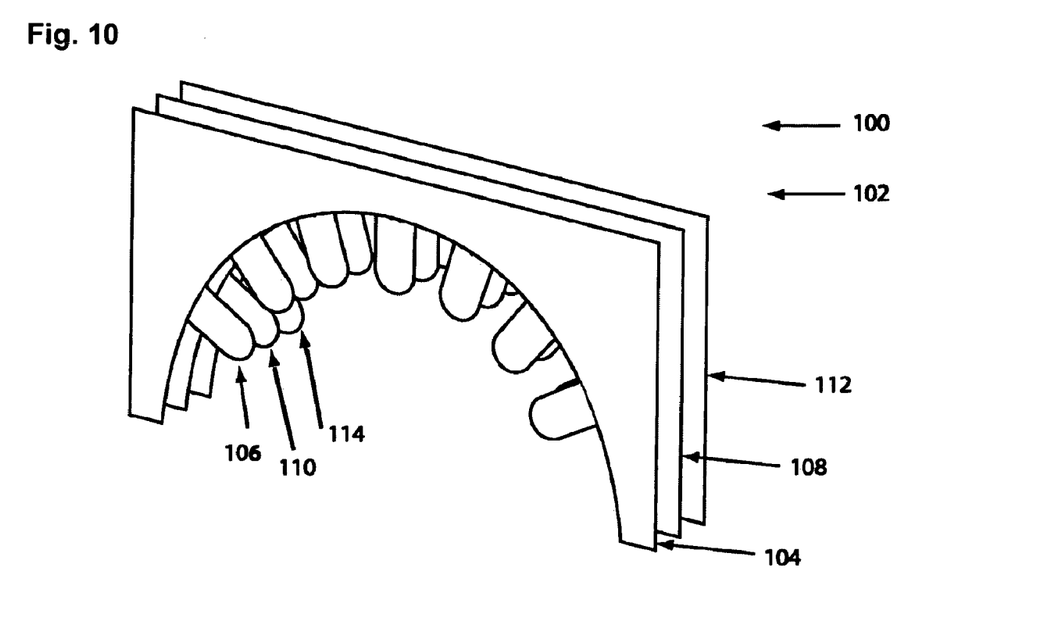
FIG. 10 schematic perspective view of a device according to another preferred embodiment of the present invention.

A device 100 according to another preferred embodiment of the invention is illustrated in FIG. 10. The device 100 comprises a light source unit 102 having a first array 104 of light emitting diodes 106, a second array 108 of light emitting diodes 110, and a third array 112 of light emitting diodes 114. The light emitting diodes 108 and 110 are hidden from view in the figure.

Each of the light emitting diodes 104, 108, and 110 are a very narrow bandwidth to improve the measurement of the at least one characteristic 12. Furthermore, and advantageously, the bandwidths are of a different range for each array 104, 108, and 112. This alters the scattering characteristics for the light scattered by the particles 20 and is particularly useful for nephelometer measurements as various characteristic such as particle size in some instances can be determined.

In the embodiment a microprocessor algorithm is used to maintain more than one specific alternative user selectable wavelength within the same configuration. In one selected mode of operation the first array 104 is operated to provide a wavelength of say 520 nm for one application, after this the microprocessor switches to the second array 108 having say alternative wavelength of 450 nm for a second application. The arrays may be embedded in one light source unit or separate light source units and, as such, may be either via the same light emitting diode array system light source, or via a concurrent light emitting diode array system light source.

Preferably the device 100 includes switching means for switching the arrays 104, 108, and 112 such that various characteristics can be determined. Each of the arrays is able to provide a Lambertian light source that that is as very close to ideal. In this manner the device 100 comprises an at least one array of spaced apart light emitting diodes, the diodes being adapted to provide a desired intensity distribution corresponding to at least one light emitting diode wavelength range.

The device 100 enables the user to quickly change the light source by switching in and out different arrays of light emitting diodes, with the same microprocessor being able to adjust accordingly for each different array. With three separate full arrays operating together increase reliability and redundancy is provided. Various operating modes involving particular selected diodes can be employed.

In normal operation, the light emitting diodes in each array are driven pulsed mode so that a relatively greater intensity output can be achieved without damaging the light emitting diodes. This is particularly advantageous as light intensity is a relatively important consideration in nephelometry.

The device 100 can be incorporated into an integrating nephelometer providing for more accurate measurement, significantly less maintenance requirements, and quicker response times, and possibly at a significantly lower cost than can be achieved with presently used light sources. The device 100 allows for different wavelengths of light without having to interchange the light source unit 16.

A control unit within the device 100 is configured to respond to both local and remote instructions where the arrays 104, 108 and 110 can be operated remotely or locally, either simultaneously or in a sequential manner.

Optical systems as used in the prior art require constant maintenance to clean the lenses and filters through which the optics are directed. In comparison the device 100 is able to provide a low maintenance long life Lambertian light source for integrating nephelometers, which have longer flash time and greater accuracy at less overall cost, with significantly less maintenance requirements.

Whilst the present invention can clearly provide advanced and significantly improved light sources for integrating nephelometers, there are also various other applications for the invention. As such, the present invention is not to be taken as being solely limited to a light source for an integrating nephelometer and may have other uses. For example, the light source may be used in a smoke detector.

Whilst the semicircular arrangement is particularly preferred for the light source unit 100, it is to be appreciated that light source unit 100 is not to be taken as being limited to the semi-circular arrangement shown in the Figures, but may be provided in the form of other physical arrangements of light emitting diodes and other light sources. There are indeed many examples of alternative light sources historically used within nephelometers and other visibility sensors to achieve a necessary fixed wavelength intensity and these light sources may be used in embodiments, in the present invention.

In this respect the use of halogen lamps has significant inherent limitations and use of a laser does certainly have the potential to provide a very narrow frequency bandwidth as a light source, but with a distinctly different type of light source with different means of operation in comparison to our the use of a light emitting diode array as described above.

Any desirable light distribution for a particular application related to particle characteristic measurement can be provided.

Figure 8:
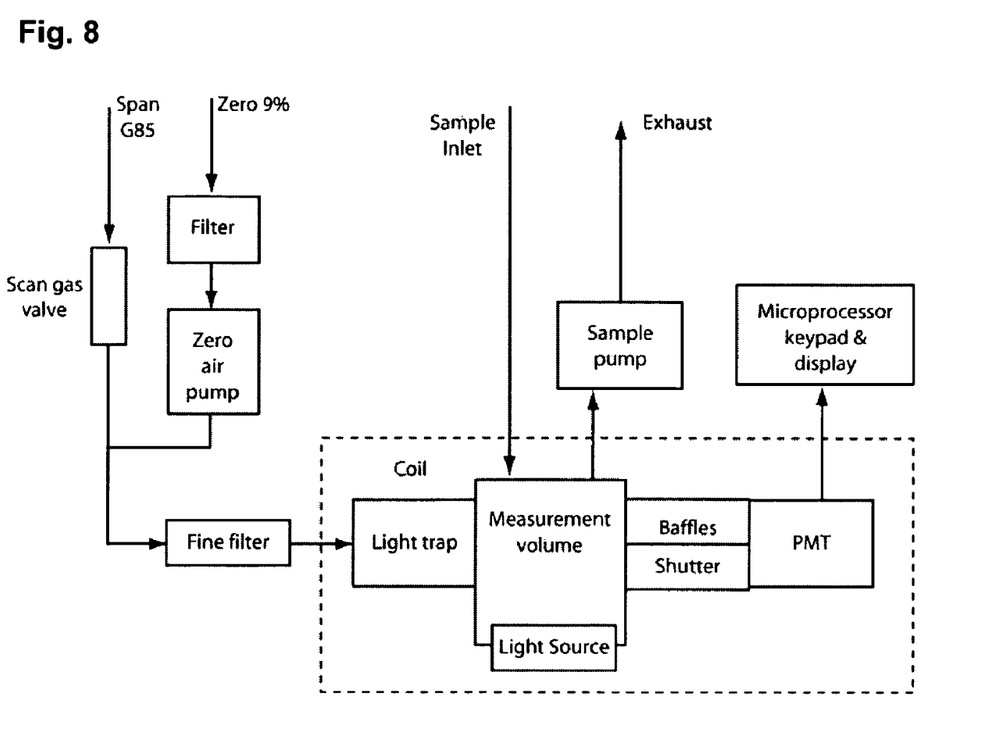
FIG. 8 is a modular view of a system incorporating the device shown in FIG. 1.
Figure 9:
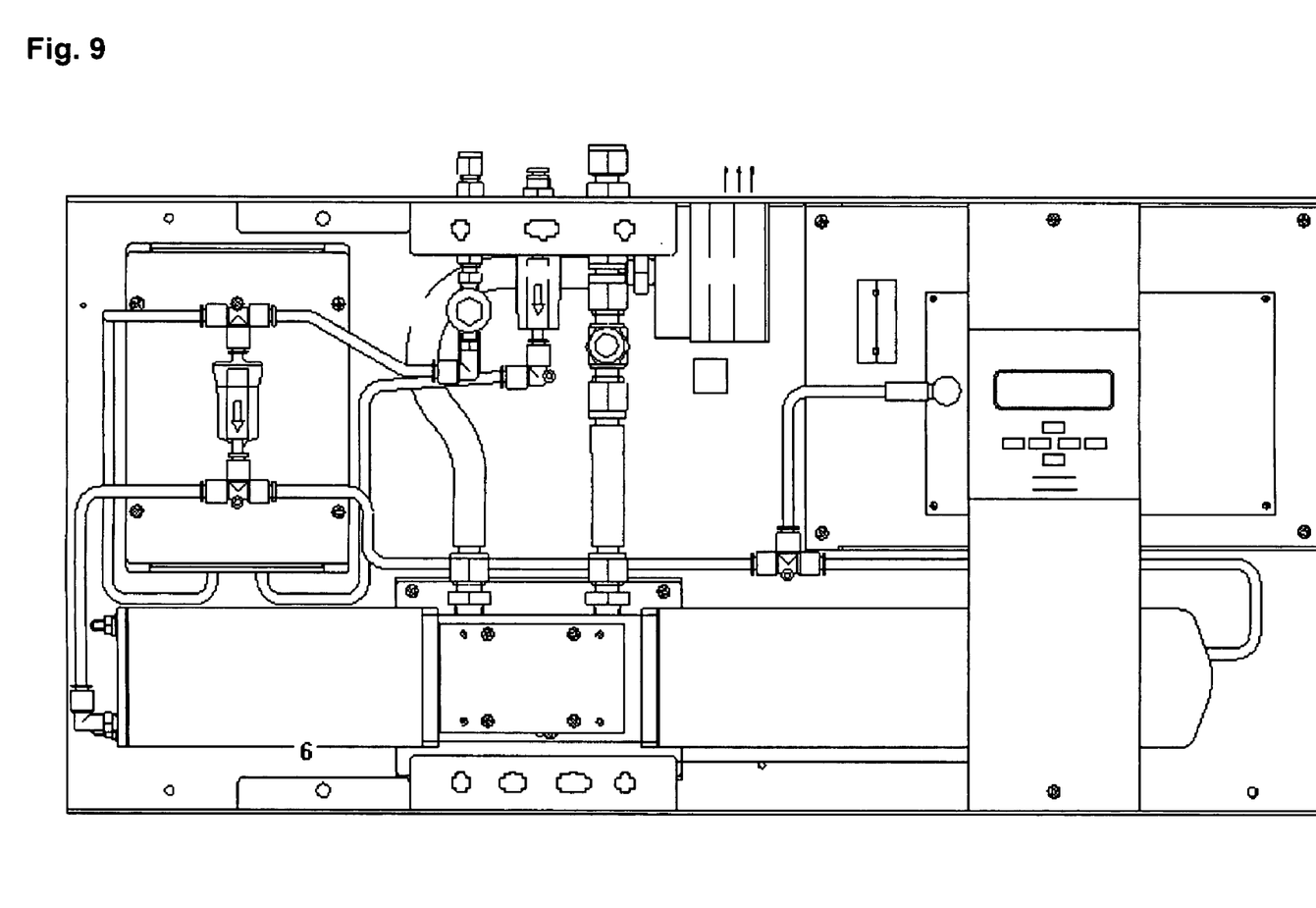
FIG. 9 is a photograph of a nephelometer embodying the system shown in FIG. 1.

FIGS. 8 and 9 show an embodiment of the present invention as used. The embodiment utilises a light source module similar to light source unit 16. The light source module is self contained and can be easily connected into the internal body of a nephelometer via a screw insertion. Light emitting diode array modules can be connected and disconnected, as different wavelength frequencies are required or a single module including a device such as device 100 can be employed.

Figure 12:
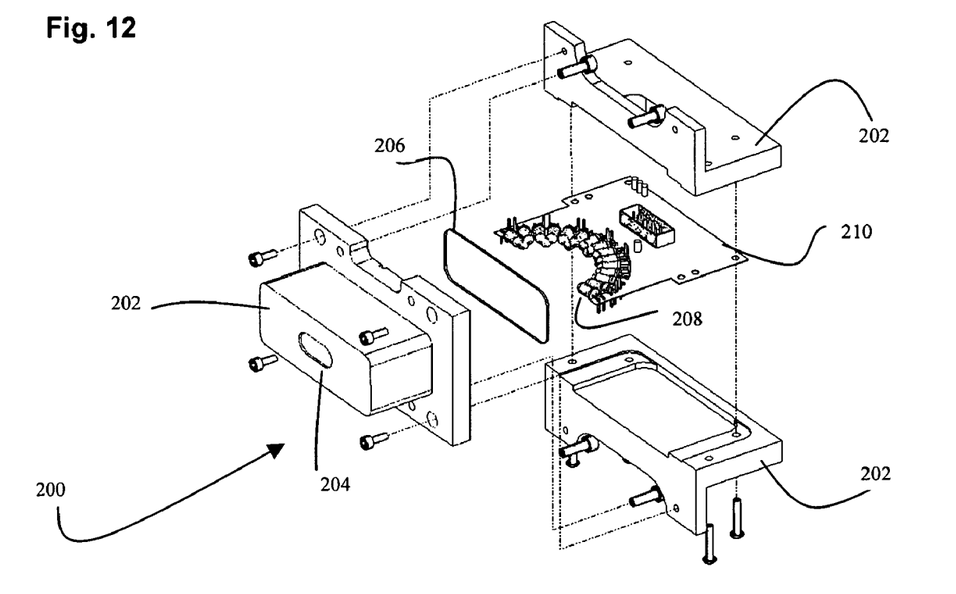
FIG. 12 is an exploded view of the light source and housing according to a further embodiment.

In FIG. 12 there is shown a light source 200 according to another preferred embodiment of the invention. The light source 200 includes a housing 202, having a window 204. The window 204 masks part of a diffuser 206 which is positioned arranged adjacent a focal point of an array of light emitting diodes 208 which form part of a printed circuit 210. The window 204 of the housing 202 serves to improve a light intensity distribution by removing emitted light not directly passing through a region surrounding the focal point 205 of the light emitting diodes 208.

Figure 13:
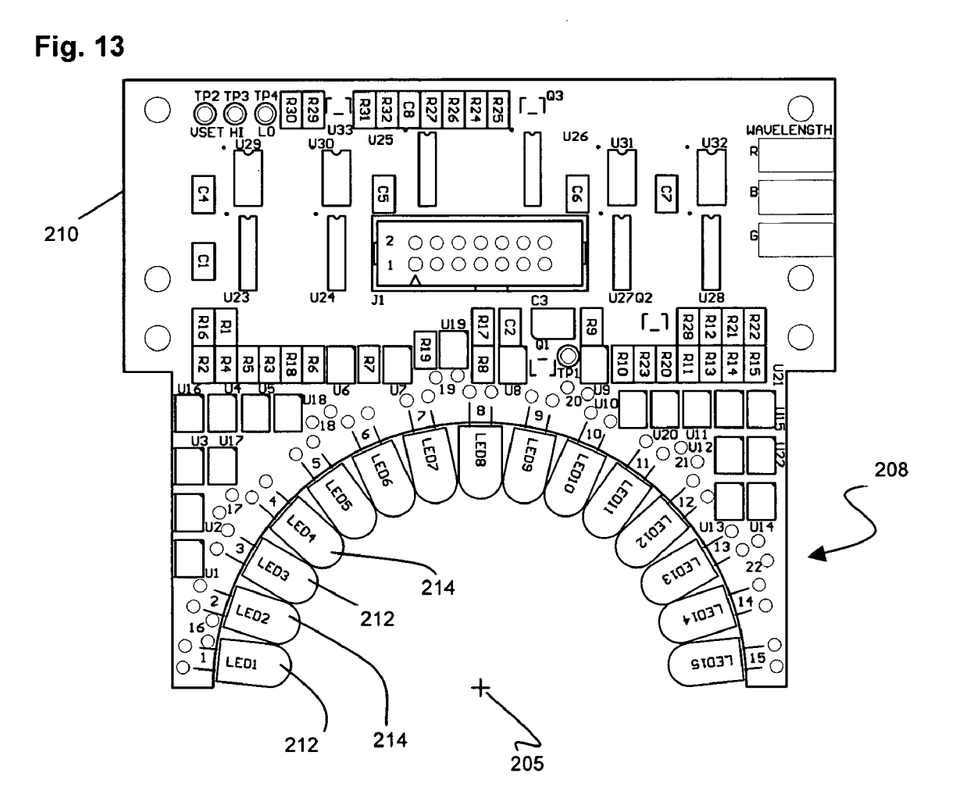
FIG. 13 is a perspective top view, in partial section, of the light source according to the embodiment shown in FIG. 12.

FIG. 13 shows the printed circuit 210 in more detail. In the circuit 210 a first group of light emitting diodes 212 are spaced in a plane along an arc, interposed among the first group of light emitting diodes 212 is a second group of light emitting diodes 214.

Figure 14:
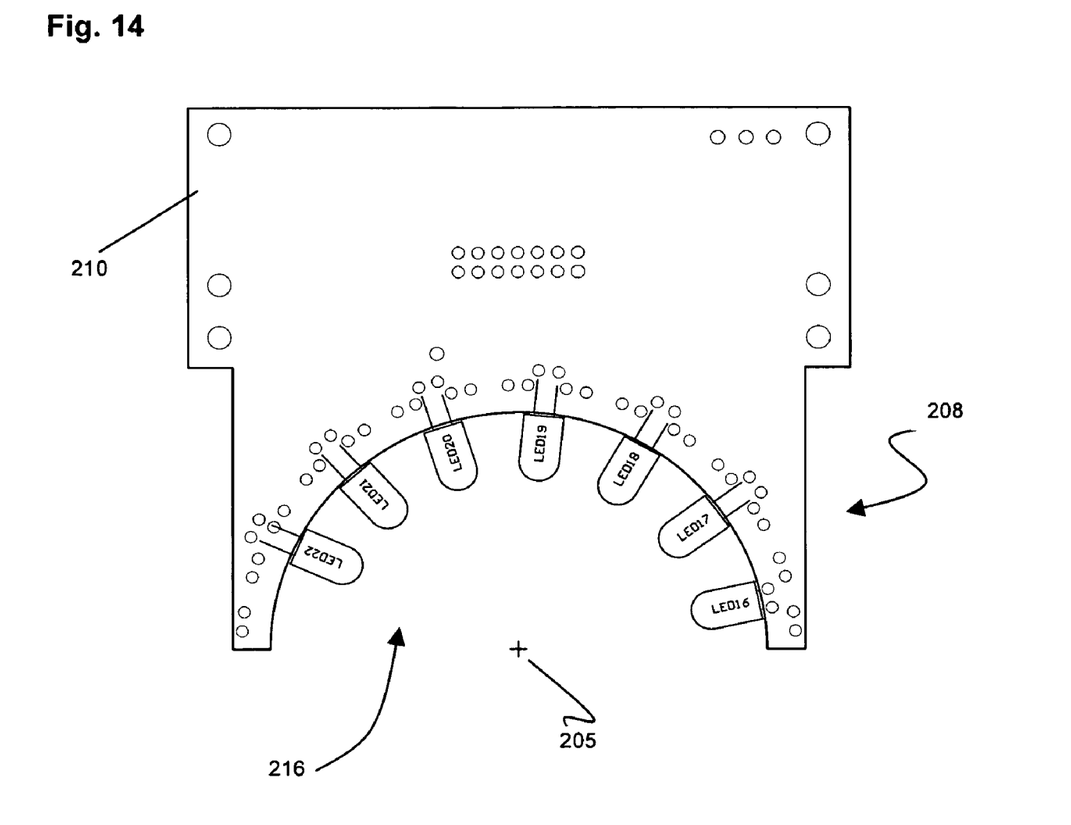
FIG. 14 is a perspective bottom view, in partial section, of the light source according to the embodiment shown in FIG. 12.

FIG. 14 shows a third group of light emitting diodes 216 forming part of the printed circuit 210. In FIG. 13 the light emitting diodes 216 are not shown for reasons of clarity. The light emitting diodes 212 and 214 are not shown in FIG. 14 for similar reasons.

Instead of using discrete resistors high precision electronic digital potentiometers are used set the intensity. In general high precision light emitting diode driver components are employed to reduce the influence of temperature variations. With the use of the temperature compensation unit, in this embodiment, no additional cooling or heat dissipation is required. Temperature is measured and compensated within a main microprocessor of a nephelometer of which device 200 forms part. The device 200 does not include a thermistor.

With single wavelength modules the particular shape of the housing 44 provides for advantageous interchangeability in which the module is easily removable and replaceable. The light source module is capable of providing a very stable light source which produces a fixed wavelength of light with a distribution that is Lambertian. This is achieved with a semi circular array of high intensity light emitting diodes, an external casing, a means for controlling, via microprocessor, the individual currents to each light emitting diode in the light emitting diode array, whereby light from each individual light emitting diode is focused to a point, which then results in a total light emission that is of a specific wavelength frequency, so that the light source can be used for precision measurement of light scattering or other applications which require a reliable precise and fixed wavelength.

Embodiments of the present invention may provide the following advantages:

(1) a Lambertian light emitting diode light source array incorporating circuitry to control the intensity of individual light emitting diodes to achieve an accurate and continuously adjustable fixed wavelength frequency light source, that is suitable for use in nephelometry, or other particle detection applications.

(2) particle characteristic discrimination without the use of various filters to achieve the necessary wavelength requirements for measuring optical properties of a sample.

(3) discrete wavelength adjustment of light emitted without using external filters through which light passes to generate required wavelengths.

(4) continuous measurement of air quality, namely more precise results due to increased flash length capabilities and more precise wavelength frequency capability.

(5) relatively minimal heating of the light source from the light emitting diodes requiring no additional cooling or heat dissipation.

(6) relatively minimal temperature variations with the use of a temperature compensation unit described.

(7) redundancy and reliability through the use of a light source compensation unit about to vary the currents in operation light emitting diodes.

(8) the ability to quickly change the light source light frequency by switching in and out different self contained arrays of light emitting diodes, with the same microprocessor being able to be reused and adjust automatically for each different array.

In arrangements an illumination is provided within a predetermined area from a plurality of sources of illumination, the intensity of at least one of the illumination sources is controlled such that the intensity of the illumination provided by the sources is substantially Lambertian.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth. For example the light source need not comprise light emitting diodes, the arrangement of the light emitting diodes may be differently shaped and may contain different quantities of light emitting diodes, different housings and diffuser arrangements may be used, the light source may be used in connection with various types of instruments, or may be used concurrently and in combination with two or more other light emitting diode arrays of differing light output wavelength frequencies.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof." Thus, unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to."

Having described the invention, the following is claimed:

1. A nephelometer device for measuring at least one characteristic of particles that are suspended in a fluid, said nephelometer device comprising:
    a light source unit for emitting light at a substantially single fixed wavelength into a region containing particles;
    wherein the light source unit is configured to emit light from a plurality of locations in a manner so that the emitted light follows a Lambertian intensity distribution, the Lambertian intensity distribution being desired for the measurement of the at least one characteristic of particles;
    a detection unit for receiving light scattered by the particles;
    wherein the light source unit comprises a plurality of spaced apart light emitting diodes;
    wherein each of the plurality of light emitting diodes are spaced apart along a semicircular arc;
    wherein the plurality of spaced apart light emitting diodes are disposed in a first array that includes a plurality of light emitting diodes each emitting substantially the same wavelength and constructed and arranged to be disposed in the same plane and evenly spaced from one light emitting diode to an adjacent one thereof;
    wherein the plurality of light emitting diodes that are disposed in the semicircular arc provide light that is emitted from the respective plurality of locations towards a focal point that is defined by the semicircular arc positioning of the plurality of light emitting diodes;
    a diffuser located at the focal point defined by the plurality of light emitting diodes for smoothing the emitted light so that the emitted light follows the Lambertian intensity distribution;
    and a control unit, the control unit for controlling the intensity the light emitted by each of the spaced apart light emitting diodes, according to the disposition of each light emitting diode, such that the emitted light is at the substantially fixed wavelength and follows the Lambertian intensity distribution, the Lambertian intensity distribution being desired for the measurement of the at least one characteristic.

2. The nephelometer of claim 1 wherein the measurement is of the particulate scattering coefficient.

3. The nephelometer of claim 1 wherein the measurement is of visibility.

4. The nephelometer of claim 1 wherein the measurement is of particulate mass concentration.

5. The nephelometer of claim 1 wherein the light source unit is for emitting light at only one fixed wavelength.

6. The nephelometer of claim 1 wherein each of the light emitting diodes emit light of a wavelength within a relatively narrow bandwidth.

7. The nephelometer of claim 6 wherein each of the light emitting diodes emits light with a light output intensity that is stable and is invariable with temperature changes.

8. The nephelometer of claim 1 wherein the light emitting diodes provide a desired intensity distribution using a selected one of plurality of light emitting diode wavelength ranges.

9. The nephelometer of claim 8 wherein the plurality of light emitting diodes have wavelength ranges that comprises a red light emitting diode wavelength range, a green light emitting diode wavelength range and a blue light emitting diode wavelength range.

10. The nephelometer of claim 1 including a temperature compensation unit for compensating for changes in the intensity of light in response to variations in temperature.

11. The nephelometer of claim 1 including a light source compensation unit for varying the intensity of light provided from each of the light emitting diodes, in response to one or more of the characteristics of the light emitting diodes changing.

12. The nephelometer of claim 1 including a light source compensation unit for turning on and off individual light emitting diodes.

13. The nephelometer of claim 1 including at least a second array of light emitting diodes.

14. The nephelometer of claim 13 wherein the wavelength of light is different for the first and second arrays.

15. The nephelometer of claim 13 including switching means for controlling the operation of the first and second arrays.

16. The nephelometer of claim 1 wherein the diffuser comprises a glass plate that is masked around the focal point and extends diametrically of the semicircular light emitting diode array.

17. The nephelometer of claim 1 wherein the plurality of light emitting diodes comprise at least three.

18. A nephelometer device for measuring at least one characteristic of particles that are suspended in a fluid, said nephelometer device comprising:
    a light source unit for emitting light at a substantially single fixed wavelength into a region containing particles;
    wherein the light source unit is configured to emit light from a plurality of locations in a manner so that the emitted light follows a Lambertian intensity distribution, the Lambertian intensity distribution being desired for the measurement of the at least one characteristic of particles;
    a detection unit for receiving light scattered by the particles;
    wherein the light source unit comprises a plurality of spaced apart light emitting diodes;
    wherein each of the plurality of light emitting diodes are spaced apart along an array formation;
    wherein the plurality of spaced apart light emitting diodes are disposed in a first array that includes a plurality of light emitting diodes each emitting substantially the same wavelength and constructed and arranged to be disposed in the same plane and evenly spaced from one light emitting diode to an adjacent one thereof;

wherein the plurality of light emitting diodes that are disposed in the array formation provide light that is emitted from the respective plurality of locations;

a diffuser having one and another sides with the one side thereof positioned directed at the plurality of light emitting diodes for smoothing the emitted light so that the emitted light follows the Lambertian intensity distribution;

a window at the another side of the diffuser in alignment with the diffuser for masking a part of the diffuser to improve the light intensity distribution;

and a control unit, the control unit for controlling the intensity the light emitted by each of the spaced apart light emitting diodes, according to the disposition of each light emitting diode, such that the emitted light is at the substantially fixed wavelength and follows the Lambertian intensity distribution, the Lambertian intensity distribution being desired for the measurement of the at least one characteristic.

19. The nephelometer of claim 18 wherein the array formation is in a semicircular arc.

20. The nephelometer of claim 19 wherein the semicircular arc provides light that is emitted from the respective plurality of locations towards a focal point that is defined by the semicircular arc positioning of the plurality of light emitting diodes.

21. The nephelometer of claim 20 wherein the diffuser is located at the focal point defined by the plurality of light emitting diodes.

22. The nephelometer of claim 21 wherein the window is disposed between the diffuser and the particles being measured.

23. The nephelometer of claim 22 wherein the placement of the window is to remove emitted light not directly passing through a region surrounding the focal point.

* * * * *